United States Patent [19]

Crutchfield et al.

[11] 4,014,959

[45] Mar. 29, 1977

[54] PHOSPHONOETHER CARBOXYLATES

[75] Inventors: Marvin M. Crutchfield, Creve Coeur, Mo.; Ludwig Maier, Kiechberg, Switzerland

[73] Assignee: Monsanto Company, St. Louis, Mo.

[22] Filed: Apr. 24, 1975

[21] Appl. No.: 571,347

[52] U.S. Cl. .................... 260/942; 252/82; 252/180; 260/932; 260/941

[51] Int. Cl.² ............................ C07C 9/40

[58] Field of Search ................... 260/942

[56] References Cited

UNITED STATES PATENTS 2,535,173  12/1950  Tawney ................. 260/942

*Primary Examiner*—Anton H. Sutto
*Attorney, Agent, or Firm*—N. E. Willis; J. E. Maurer; H. B. Roberts

[57] ABSTRACT

Phosphonoether carboxylate esters and acids are intermediates for phosphonoether carboxylate salts useful as sequestering agents.

3 Claims, No Drawings

PHOSPHONOETHER CARBOXYLATES

BACKGROUND OF THE INVENTION

This invention relates to novel phosphonoether carboxylates. The esters and acid forms of the compounds are useful as intermediates to salts useful as sequestrants for various metal and alkaline earth metal ions (particularly ions such as calcium and magnesium ions which contribute to water "hardness").

The value of sequestrants in various industrial and domestic water treating and cleaning applications is well understood by those skilled in the art. It is further recognized that the provision of novel sequestering agents to permit selection of optimum sequestering compounds and formulations for particular applications is a continuing need of the art.

SUMMARY OF THE INVENTION

It is an object of the present invention to provide novel sequestrant compounds and novel intermediate compounds useful for preparing such sequestrants.

The compounds by which this objective is achieved are phosphonoether carboxylates whose structure, synthesis and use will be understood from the following description of the preferred embodiments.

DESCRIPTION OF THE PREFERRED EMBODIMENTS

The ester forms of the compounds of the present invention can be represented by the formula

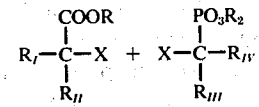

In the above formula, R represents benzyl, or an alkyl group containing from 1 to 4 carbon atoms; $R_I$ represents hydrogen, an alkyl group containing from 1 to 3 carbon atoms, $CH_2PO_3R_2$ or $CH_2COOR$; $R_{II}$ represents hydrogen, an alkyl group containing from 1 to 3 carbon atoms, $CH_2COOR$, $CH_2PO_3R_2$ or $COOR$; $R_{III}$ represents hydrogen, an alkyl group containing from 1 to 3 carbon atoms, $CH_2COOR$ or $CH_2PO_3R_2$; and $R_{IV}$ represents hydrogen, an alkyl group containing from 1 to 3 carbon atoms, $CH_2PO_3R_2$, $CH_2COOR$ or $PO_3R_2$. At least one of $R_I$, $R_{II}$, $R_{III}$ and $R_{IV}$ must be $COOR$, $CH_2COOR$, $PO_3R_2$ or $CH_2PO_3R_2$.

Preferred compounds of the invention are those in which $R_I$ is hydrogen, an alkyl group containing 1 to 3 carbon atoms or $CH_2COOR$; $R_{II}$ is hydrogen, an alkyl group containing 1 to 3 carbon atoms, $CH_2COOR$ or $COOR$, $R_{III}$ is hydrogen, an alkyl group containing 1 to 3 carbon atoms, or $CH_2PO_3R_2$; and $R_{IV}$ represents hydrogen, an alkyl group containing from 1 to 3 carbon atoms, $CH_2PO_3R_2$ or $PO_3R_2$.

These compounds can be prepared by a Williamson ether type synthesis reacting:

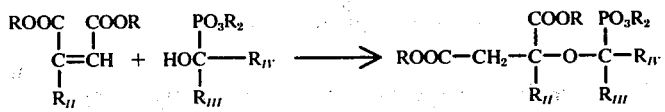

where X in one reactant is -O alkali metal and in the other is -Cl or -Br.

Alternatively, compounds wherein one of $R_I$ and $R_{II}$ is $CH_2COOR$ or one of $R_{III}$ and $R_{IV}$ are $CH_2PO_3R_2$ may, in some instances, be more readily prepared by a Michael-type Addition to a double bond of an appropriate unsaturated starting material.

For example:

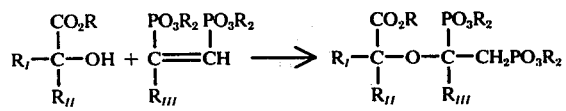

This is particularly preferred when $R_1$ is $CH_2COOR$. Similarly, the reaction

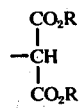

is preferred when $R_{IV}$ is $CH_2PO_3R_2$.

Conversion of the ester forms of the compounds to acid forms is accomplished by acidulation with a strong acid, e.g. HCl, $H_2SO_4$, etc. The alkali metal, ammonium or amine salt forms can be obtained by neutralization of the acids or by reacting the ester with a strong base (saponification). The tendency of substituted malonates to undergo

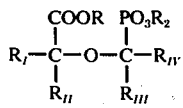

decarboxylation during long acid hydrolysis conditions makes conversion of such ester to the corresponding acid form somewhat difficult. This difficulty may be avoided by hydrolysis of compounds containing such malonate ester groups under basic conditions of hydrolysis (saponification) to obtain the salt form directly. Since one of the R groups in the $-PO_3R_2$ ester moiety is resistant to saponification, in some instances partial ester salts can be obtained. It is noted, however, that such partial salts containing one unhydrolyzed ester groups per phosphorus have useful sequestering properties, even though the fully hydrolyzed compounds are usually preferred. Fully neutralized salt forms of the compounds can often be conveniently obtained by hydrogenation of benzyl ester forms

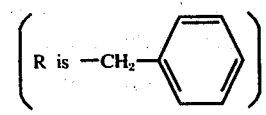

of the compounds in the presence of a palladium on charcoal catalyst followed by neutralization of the hydrogenated product with a base.

As indicated, the total or partial salt compounds of the invention are sequestrants which can be used in conventional manner in a variety of applications. For example, such sequestrants are useful as water softeners and, in some instances, as scale inhibitors or as detergency builders. The invention is further illustrated by the following examples:

EXAMPLE I

A solution of 38 gms of $$(CH_3CH_2O)_2-\overset{O}{\underset{\|}{P}}-CH_2ONa$$

in 150 ml. bis (2-methoxy ethyl) ether is prepared by reacting 0.2 moles of diethylphosphite with 0.2 moles sodium in bis (2-methoxyethyl) ether and adding 0.2 moles paraformaldehyde. About 51 gms of $$CH_3-\underset{\underset{COOCH_2CH_3}{|}}{\overset{\overset{COOCH_2CH_3}{|}}{C}}-Br$$

is then added to the solution over a period of about ½ hour, the temperature being maintained between 25°–30° C. The mixture is then refluxed for one hour, allowed to stand about 16 hours, and filtered. The filtrate is distilled, the product $$H_5C_2O-\underset{\underset{OC_2H_5}{|}}{\overset{\overset{O}{\|}}{P}}-CH_2-O-\underset{\underset{COOC_2H_5}{|}}{\overset{\overset{COOC_2H_5}{|}}{C}}-CH_3$$

being obtained at 114°–121.5° C., 0.05 mm Hg. The product is a colorless liquid having a refractive index, $n_D^{20}$ 1.4381 and exhibiting the nuclear magentic resonance spectrum shown in table 1 following the examples.

0.05 moles of the above ester is reacted with 0.15 moles of NaOH solution followed by evaporation to dryness. The product obtained is the partial ester salt.

$$NaO\underset{\underset{C_2H_5}{|}}{\overset{\overset{O}{\|}}{P}}-CH_2-O-\underset{\underset{CO_2Na}{|}}{\overset{\overset{CO_2Na}{|}}{C}}-CH_3$$

The above salt is tested for sequestration function (according to the procedure described by Matzner et al., Tenside, 10, 119–25; 239–245 (1973)) and found to effectively sequester calcium ions.

EXAMPLE II

A solution of 48 gms $$HC\underset{\underset{CH_3}{|}}{\overset{\overset{CH_3}{|}}{-}}-O-\underset{\underset{O}{|}}{\overset{\overset{O}{\|}}{P}}-CH_2ONa$$
$$\underset{CH_3-CH-CH_3}{}$$

in 150 ml. bis (2-methoxy ethyl) ether is prepared by reacting 0.2 mole diisopropylphosphite, 0.2 mole sodium, and 0.2 mole paraformaldehyde. About 51 gms $$CH_3-\underset{\underset{COOC_2H_5}{|}}{\overset{\overset{COOC_2H_5}{|}}{C}}-Br$$

is added to the solution over a period of about 20 minutes while maintaining the temperature at about 35° C. The mixture is then refluxed for 2 hours, allowed to stand about 16 hours, and filtered.

Solvent is distilled from the filtrate which is then again filtered to remove precipitated solids. The filtrate product $$\underset{\underset{CH_3-CH-CH_3}{}}{\overset{CH_3}{\underset{|}{CH}}-O}-\overset{\overset{O}{\|}}{\underset{\underset{O}{|}}{P}}-CH_2-O-\underset{\underset{COOC_2H_5}{|}}{\overset{\overset{COOC_2H_5}{|}}{C}}-CH_3$$

is a clear liquid having the nuclear magnetic resonance spectrum shown in table 1 following the examples.

About 9.2 grams of the above ester product is added to 3 grams sodium hydroxide in 110 ml. ethanol and the mixture is refluxed for 10 hours. The alcohol is then evaporated from the mixture, the residue dissolved in water, and dimethylformamide added. After 48 hours, white crystals of $$\underset{\underset{CH_3}{|}}{\overset{CH_3}{\underset{|}{CHO}}}-\overset{\overset{O}{\|}}{\underset{\underset{ONa}{|}}{P}}-CH_2-O-\underset{\underset{COONa}{|}}{\overset{\overset{COONa}{|}}{C}}-CH_3$$

product salt precipitate. The product salt exhibits the nuclear magnetic resonance spectrum shown in table 1 following the examples and, when tested for sequestration function according to the procedure referenced in Example I, is found to effectively sequester calcium ions.

EXAMPLE III

About 0.2 mole maleic acid diethyl ester is added to a solution of 0.2 mole $$H_5C_2-O-\underset{\underset{OC_2H_5}{|}}{\overset{\overset{O}{\|}}{P}}-CH_2ONa$$

dissolved in 100 ml. bis (2-methoxy ethyl) ether, the mixture being maintained at about 25° C. The mixture is refluxed for 4 hours, treated with 0.2 mole acetic acid and distilled to separate

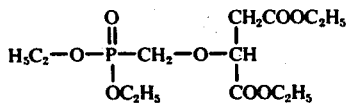

as a colorless oil.

The above ester product is hydrolyzed by reflux with concentrated hydrochloric acid for 8 hours to yield

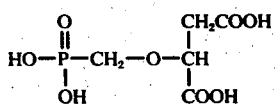

The salt of this acid obtained by neutralization with sodium hydroxide is found to effectively sequester calcium ions when tested according to the procedure referenced in Example I.

EXAMPLE IV

About 0.1 mole of

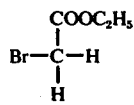

is slowly added to 0.1 mole of

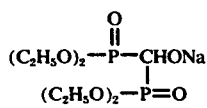

in 50 ml. bis (2-methoxy ethyl) ether and the resulting mixture is refluxed for 3 hours. Precipitated NaBr is separated and the filtrate distilled to separate

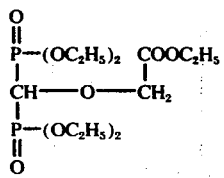

product.

This product is hydrolyzed by refluxing in concentrated hydrochloric acid for 10 hours to yield the acid

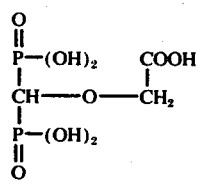

The salt obtained by neutralization of the above acid is an effective sequestrant for calcium ions.

EXAMPLE V

A solution of 0.5 mole

in tetrahydrofuran is added to 0.5 mole ethene -1,2 - diphosphonate - ethylester. The resulting mixture is refluxed for 10 hours, treated with 0.5 mole acetic acid and distilled to separate the ester product

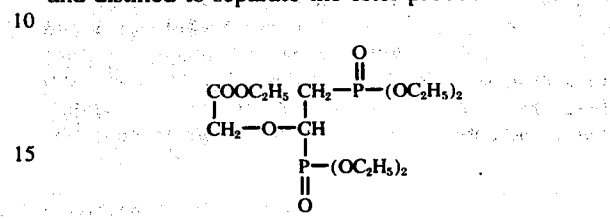

This ester product is hydrolyzed by refluxing in concentrated hydrochloric acid to yield the acid product.

The salt of the above acid product obtained by neutralization with sodium hydroxide is an effective sequestrant for calcium ions.

EXAMPLE VI

About 0.2 moles

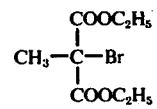

is slowly added to a solution of 0.2 moles

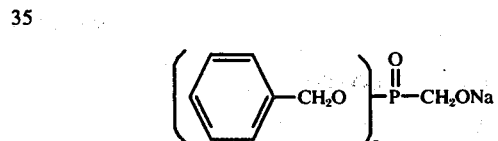

in 150 ml. bis (2-methoxy ethyl) ether while maintaining the temperature at about 35° C. The mixture is then refluxed for 2 hours, allowed to stand 16 hours, and filtered. Solvent is distilled from the filtrate to leave a clear liquid ester product

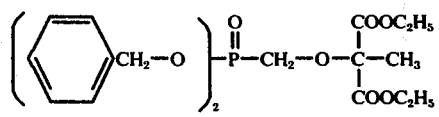

This ester product is dissolved in ethanol and hydrogenated in the presence of a palladium on charcoal (5% by weight palladium) catalyst. The catalyst is separated by filtration and ethanol evaporated leaving the acid product

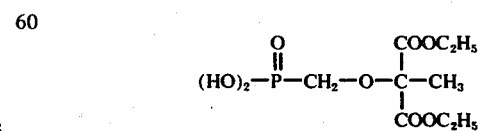

Reaction of this acid product with sodium hydroxide in ethanol (2 hours reflux) and evaporation of the ethanol yields the salt product

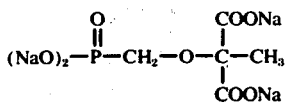

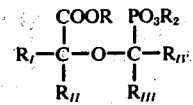

as a white solid. This salt product is an effective sequestrant.

Table I below shows nuclear magnetic resonance spectra of representative compounds of the invention.

In the table, coupling constants (J with subscripts indicating specific nuclei coupled) are expressed in hertz; H represents proton count; t, d, and qu, respectively, indicate triplets, doublets and quadruplets.

wherein R is selected from the group consisting of alkyl groups containing from 1 to 4 carbon atoms and benzyl; $R_I$ is selected from the group consisting of hydrogen, alkyl groups containing from 1 to 3 carbon atoms, and $CH_2COOR$; $R_{II}$ is selected from the group consisting of hydrogen, alkyl groups containing from 1 to 3 carbon atoms, $CH_2COOR$ and COOR; $R_{III}$ and $R_{IV}$ each are selected from the group consisting of hydrogen, alkyl groups containing from 1 to 3 carbon atoms and $CH_2COOR$; at least one of $R_I$, $R_{II}$, $R_{III}$, and $R_{IV}$ being COOR or $CH_2COOR$.

2. A compound according to claim 1 wherein R is benzyl.

3. A compound according to claim 2 wherein $R_I$, $R_{III}$ and $R_{IV}$ are hydrogen.

| | a | b | c | d | e |
|---|---|---|---|---|---|
| PHOSPHORUS-31-AND HYDROGEN-1-NMR SPECTRA IN PPM ($^1$H-NMR - trimethyl silane reference) | | | | | |
| $(CH_3CH_2O)_2PCH_2OC(CH_3)(CO_2CH_2CH_3)_2$<br>a' d c b e a $CCl_4$ | 1.28 (t)<br>a':1.32 (t)$^{12H}$ | 1.57(s,2.85H) | 3.87(d,$J_{PCH}$10.8)<br>c+d+e = 10.1H | 4.07<br>(2 qu) | 4.21 (qu) |
| Eu(DPM)$_3$ | 1.5(t,6.1H)<br>a':2.68(t,6.02H) | | | | 4.50<br>(qu,4.05H)<br>4.7 |
| $[(CH_3)_2CHO]_2PCH_2OC(CH_3(CO_2CH_2CH_3)_2$<br>a e c b d a $CCl_4$ | 1.30<br>(m,18.7H) | 1.55(s,2.7H) | 3.78(d,$J_{PCH}$10.6)<br>c+d+e = 7.6H | 4.2(qu) | |
| NaO O<br>\\\\ ||<br>/PCH$_2$OC(CH$_3$) 2Na)$_2$<br>(CH$_3$)$_2$CHO<br>a d c b D$_2$O | 1.25(d,J6:<br>6.08H) | 1.47(s,2.95H) | 3.47(d,J11:<br>2.08H) | 4.5<br>(m,0.86H) | |
| ($^{31}$P-NMR - 85% H$_3$PO$_4$ reference) | | | | | |
| $(CH_3CH_2O)_2PCH_2OC(CH_3)(CO_2CH_2CH_3)_2$<br>a' d c b e a $CCl_4$ | | | | −19.0<br>(subst.) | |
| $[(CH_3)_2CHO]_2PCH_2OC(CH_3)(CO_2CH_2CH_3)_2$<br>a e c b d a $CCl_4$ | | | | −17<br>(subst.) | |
| NaO O<br>\\\\ ||<br>/PCH$_2$OC(CH$_3$)(CO$_2$Na)$_2$<br>(CH$_3$)$_2$CHO<br>a d c b D$_2$O | | | | −17.5<br>(in H$_2$O) | |

What is claimed is:

1. A compound represented by the formula: